(12) United States Patent
Trafalis

(10) Patent No.: US 10,513,529 B2
(45) Date of Patent: Dec. 24, 2019

(54) 1,2,4-TRIAZOLO-[3,4-B]-1,3,4-THIADIAZOLE DERIVATIVES

(71) Applicants: GALENICA S.A., Kifissia (GR); ENERGONBIO TECHNOLOGIES S.A., Nikaia (GR)

(72) Inventor: Dimitrios Trafalis, Nikaia (GR)

(73) Assignees: GALENICA S.A., Kifissia (GR); ENERGONBIO TECHNOLOGIES S.A., Nikaia (GR)

( * ) Notice: Subject to any disclaimer, the term of this patent is extended or adjusted under 35 U.S.C. 154(b) by 0 days.

(21) Appl. No.: 16/317,341

(22) PCT Filed: Jul. 14, 2017

(86) PCT No.: PCT/EP2017/067908
§ 371 (c)(1),
(2) Date: Jan. 11, 2019

(87) PCT Pub. No.: WO2018/011414
PCT Pub. Date: Jan. 18, 2018

(65) Prior Publication Data
US 2019/0194228 A1   Jun. 27, 2019

(30) Foreign Application Priority Data

Jul. 14, 2016 (GR) .............................. 20160100380

(51) Int. Cl.
*C07D 513/04* (2006.01)
*A61P 35/00* (2006.01)

(52) U.S. Cl.
CPC ............ *C07D 513/04* (2013.01); *A61P 35/00* (2018.01)

(58) Field of Classification Search
CPC ............................... C07D 513/04; A61P 35/00
USPC ........................................................ 514/338
See application file for complete search history.

(56) References Cited

FOREIGN PATENT DOCUMENTS

| WO | 2007/034510 A1 | 3/2007 |
|---|---|---|
| WO | 2007/064797 A2 | 6/2007 |
| WO | 2008/060578 A2 | 5/2008 |
| WO | 2008/144767 A1 | 11/2008 |
| WO | 2010/138663 A1 | 12/2010 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17 , 91-106 (Year: 1998).*
Golub et al., Molecular Classification of Cancer: Class Discovery and Class Prediction by Gene Expression Monitoring, Science (1999), vol. 286, 531-537 (Year: 1999).*
Holla, B.S., Shivananda, M.K., Akberali, P.M., Baliga, S., Safeer, S., Farmaco, 1996, 51, 785.
Zhang, Z.Y., Sum, X.W., Chu, C.H., Zhao, L., J. Chim. Chem. Soc., 1997, 44, 535.
Demirbas, N., Demirbas, A., Karaoglu, S.A., Celik, E., Arkivoc., 2005, 1, 75.
Ibrahim, D.A., "Synthesis and Biological Evaluation of 3,6-disbstituted [1,2,4]triazolo [3,4-b][1,3,4]Thiadiazole Derivatives as a Novel Class of Potential Anti-tumor Agents" European Journal of Medicinal Chemistry, Editions Scientifique Elsevier, Paris, France, vol. 44, No. 7, Jul. 1, 2009 pp. 2776-2781.
Al-Masoudi, N.A., Al-Soud, Y.A., Nucleos:Nucleot. Nucleic Acids, 2008, 27, 1034.
Chowrasia, D., Karthikeyan, C., Choure, L., Sahabjada, Gupta, M., Arshad, Md., Trivedi, P., Arab. J. of Chem., 2013, doi:10.1016/j.arabjc.2013.08.026.
Ilango, K. et al., "Facile synthesis and Cytotoxic Activity of 3,6-disubstituted 1,2,4-triazolo-[3,4-b]-1,3,4-thiadiazoles", European Journal of Chemistry, vol. 1, No. 1, Jan. 1, 2010, pp. 50-53.
Kritsanida, M., Mouroutsou, k, Marakos, P., Pouli, N., Papakonstantinou-Garoufalias, S., Pannecouque, C., Witvrouw, M., Declercq, E., Farmaco, 2002, 57, 253.
Invidiata, F.P., Simoni, D., Skintu, F., Pinna, N., Farmaco., 1996, 51, 659.
Srivastava, V., Sen, S., Shekar, R., Indian J. Chem., 1994, 33B, 344.
Chawla, G., Kumar, U., Bawa, S., Kumar, J., J. Enzyme Inhib. Med. Chem., 2012, 27, 658.
Amir, M., Harish, K., Javed, S.A., Eur. J. Med. Chem., 2008, 43, 2056.
Prasad, A.R., Ramlingam, T., Bhaskar Rao A., Diwan, P.B., Sattur., Indian J. Chem., 1986, 25B, 566.
Chawla, G., Kumar, U., Bawa, S., Kumar, J., J. Enzyme Inhib. Med. Chem., 2012, 27, 65.
Karabasanagouda, T., Adhikari, A.V., Suchethasettey, N., Eur. J. Med. Chem., 2007, 42, 521.
Tiwari, N., Chaturvedi, B., Nizamuddin., Agric. Biol. Chem., 1988, 52, 1229.

(Continued)

*Primary Examiner* — Kristin A Vajda
(74) *Attorney, Agent, or Firm* — David & Bujold PLLC; Michael J. Bujold

(57) ABSTRACT

Derivatives of 1,2,4-Triazolo-[3,4-b]-1,3,4-thiadiazoles according to formula (I), as set forth below:

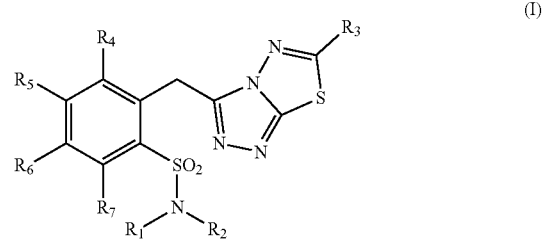

(I)

processes for production thereof, pharmaceutical compositions containing the same and the use thereof in treatment of cancer.

15 Claims, No Drawings

(56) References Cited

OTHER PUBLICATIONS

Ei-Khawass, S.M., Khalil, M.A., Hazzaa, A.A., Bassiouny, H.A., Loutfy, N.F., Farmaco. 1989, 44, 703.2. Imitiaz, M., Kumar, V., Indian J. Chem., 1992, 31B, 673.
Hill, D.L. Cancer Chemother. Pharmacol. 1980, 4, 215.
Nelson, J.A., Rose, L.M., Benette, L. Cancer Res. 1977, 37, 182.
Tsukamoto, K., Suno, M., Igarashi, K., Kozai, Y., Sugino, Y., Cancer Res. 1975, 35, 2631.
See International Search Report Corresponding to PCT/EP2017/067908 dated Sep. 6, 2017.
Written Opinion Corresponding to PCT/EP2017/067908 dated Sep. 6, 2017.
Subrahmanya, B., "Synthesis of Some New 1,2,4-Triazolo[3,4-b]-Thiadiazole Derivatives as Possible Anticancer Agents", Phosphorus and Sulfur and the Related Elements, Gordon and Breach—Harwood Academic, CH, vol. 179, Jan. 1, 2004, pp. 1595-1603.

* cited by examiner

1,2,4-TRIAZOLO-[3,4-B]-1,3,4-THIADIAZOLE DERIVATIVES

TECHNICAL FIELD OF THE INVENTION

The present invention relates to new 1,2,4-triazolo-[3,4-b]-1,3,4-thiadiazole derivatives, their methods of production and use in cancer treatment.

BACKGROUND OF THE INVENTION

Cancer still remains a fatal health problem even if progress in therapeutics has been noted. Nowadays, a constant increase in deaths from different types of cancer has been observed and it is estimated that in 2030 deaths will reach 12 million. Usually, anticancer therapy is considered as a challenge because of its high toxicity which accompanies it. Main side effects of anticancer drugs are nausea, vomiting, diarrhea, alopecia and infections (which are usually caused by leukopenia). Consequently, the development of new no or less toxic active anticancer drugs is of the utmost importance and necessity.

Heterocyclic compounds that include thiazolic or thiadiazolic chemical structures have shown very important biologic activities such as antibacterial [a] Holla, B.S., Shivananda, M. K., Akberali, P. M., Baliga, S., Safeer, S., Farmaco, 1996, 51, 785. b) Zhang, Z. Y., Sum, X. W., Chu, C. H., Zhao, L., J. Chim. Chem. Soc., 1997, 44, 535. c) Demirbas, N., Demirbas, A., Karaoglu, S. A., Celik, E., Arkivoc., 2005, 1, 75.], anticancer [a] Ibrahim, D. A., Eur. J. Med. Chem., 2009, 44, 2776 b) Al-Masoudi, N. A., Al-Soud, Y. A., Nucleos:Nucleot. Nucleic Acids, 2008, 27, 1034. c) Chowrasia, D., Karthikeyan, C., Choure, L., Sahabjada, Gupta, M., Arshad, Md., Trivedi, P., Arab. J. of Chem., 2013, doi:10.1016/j.arabjc.2013.08.026. d) Ilango, K., Valentina, P., Eur. J. Chem., 2010, 1, 50.], antiviral [a) Kritsanida, M., Mouroutsou, A., Marakos, P., Pouli, N., Papakonstantinou-Garoufalias, S., Pannecouque, C., Witvrouw, M., Declercq, E., Farmaco, 2002, 57, 253. b) Invidiata, F. P., Simoni, D., Skintu, F., Pinna, N., Farmaco., 1996, 51, 659. c) Srivastava, V., Sen, S., Shekar, R., Indian J. Chem., 1994, 33B, 344.], anti-inflammatory [a) Chawla, G., Kumar, U., Bawa, S., Kumar, J., J. Enzyme Inhib. Med. Chem., 2012, 27, 658. b) Amir, M., Harish, K., Javed, S. A., Eur. J. Med. Chem., 2008, 43, 2056. c) Prasad, A. R., Ramlingam, T., Bhaskar Rao A., Diwan, P. B., Sattur., Indian J. Chem., 1986, 25B, 566.], analgesic [a) Srivastava, V., Sen, S., Shekar, R., Indian J. Chem., 1994, 33B, 344. b) Chawla, G., Kumar, U., Bawa, S., Kumar, J., J. Enzyme Inhib. Med. Chem., 2012, 27, 658.], antifungal [a) Karabasanagouda, T., Adhikari, A. V., Suchethasettey, N., Eur. J. Med. Chem., 2007, 42, 521. b) Tiwari, N., Chaturvedi, B., Nizamuddin., Agric. Biol. Chem., 1988, 52, 1229.] and anthelmintic [α) El-Khawass, S.M., Khalil, M. A., Hazzaa, A. A., Bassiouny, H. A., Loutfy, N. F., Farmaco. 1989, 44, 703. 2. lmitiaz, M., Kumar, V., Indian J. Chem., 1992, 31B, 673.]. In older studies, some amino- and diimino thiadiazole derivatives have shown anticancer activity [a) Hill, D. L. Cancer Chemother. Pharmacol. 1980, 4, 215. b) Nelson, J. A., Rose, L. M., Benette, L. Cancer Res. 1977, 37, 182. c) Tsukamoto, K., Suno, M., Igarashi, K., Kozai, Y., Sugino, Y., Cancer Res. 1975, 35, 2631].

SUMMARY OF THE INVENTION

The present invention provides new 1,2,4-triazolo-[3,4-b]-1,3,4-thiadiazole derivatives and their pharmaceutically acceptable salts, their methods of production and biologic activity. The compounds of the present invention can be applied in anticancer therapies due to their anticancer activity which is accompanied by low acute toxicity.

DETAILED DESCRIPTION OF THE INVENTION

The present invention provides 1,2,4-triazolo-[3,4-b]-1,3,4-thiadiazoles of formula (I) or pharmaceutically acceptable salts thereof

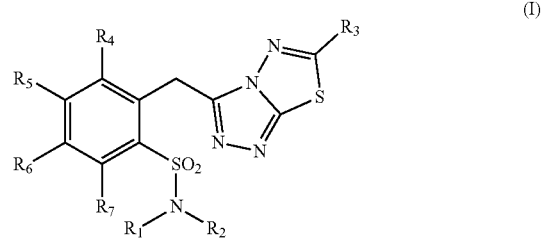

(I)

wherein, $R_1$ and $R_2$ are the same or different and are selected from the group consisting of $C_1$-$C_5$ alkyl, phenyl, methylphenyl, $R_3$ is selected from the group consisting of $CH_2R_8$, $CH_2CH_2R_8$, $CH=CHR_8$, $CH_2CH_2CH_2R_8$, $CH_2CH=CHR_8$, $CH=CHCH_2R_8$, $CH=CH-OR_8$, $CH_2-OR_8$, $CH_2CH_2-OR_B$, $CH=CH-NHR_8$, $CH_2-NHR_8$, $CH_2CH_2-NHR_8$, $CH=CH-SR_8$, $CH_2-SR_8$, $CH_2CH_2-SR_8$,

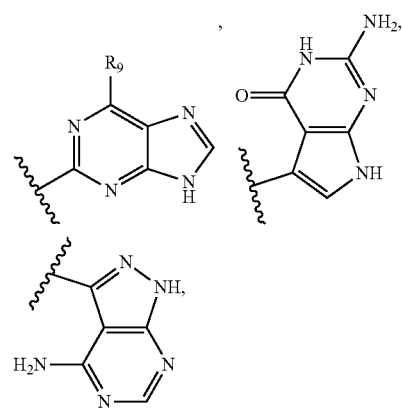

substituted or unsubstituted phenyl, benzyl, pyridyl, pyrimidinyl, triazinyl, triazinanyl, oxazinyl, oxazinanyl, cyclohexanyl, cyclohexenyl, cyclohexadienyl, pyranyl, oxathianyl, piperidinyl, cyclopentanyl, cyclopentenyl, cyclopentadienyl, pyrrolidinyl, pyrrolyl, furanyl, oxazolidinyl, pyrazolidinyl, thiophenyl, oxathiinyl, oxathiolyl, oxathiolanyl, wherein the substituent or substituents are selected from the group consisting of methyl F, Cl, Br, I, $NO_2$, CN, $NH_2$, $OCH_2X$, $CH_2X$, $CX_3$, $CH_2CH_2X$, OH wherein X is selected from the group consisting of H, F, Cl, Br, I, $R_4$, $R_5$, $R_6$, $R_7$ are the same or different and are selected from the group consisting of H, F, Cl, Br, I, $NO_2$, CN, $NH_2$, $OCH_3$, OH, $NHCH_2CH_3$, $N(CH_3)_2$, $R_8$ is selected from the group consisting of

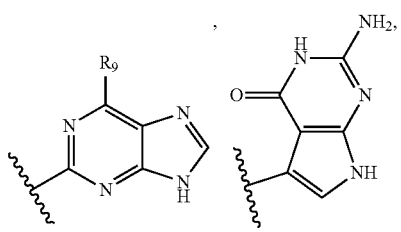
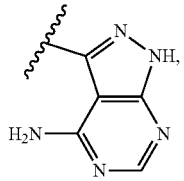

substituted or unsubstituted phenyl, benzyl, pyridyl, pyrimidinyl, triazinyl, triazinanyl, oxazinyl, oxazinanyl, cyclohexanyl, cyclohexenyl, cyclohexadienyl, pyranyl, oxathianyl, piperidinyl, cyclopentanyl, cyclopentenyl, cyclopentadienyl, pyrrolidinyl, pyrrolyl, furanyl, oxazolidinyl, pyrazolidinyl, thiophenyl, oxathiinyl, oxathiolyl, oxathiolanyl, wherein the substituent or substituents are selected from the group consisting of methyl F, Cl, Br, I, $NO_2$, CN, $NH_2$, $OCH_2X$, $CH_2X$, $CX_3$, $CH_2CH_2X$, OH wherein X is selected from the group consisting of H, F, Cl, Br, I, $R_9$ is selected from the group consisting of $NHR_{10}$, $NR_{11}R_{12}$, $R_{10}$ is selected from the group consisting of $C_1$-$C_5$alkyl, phenyl, $R_{11}$ and $R_{12}$ are the same or different and they are $C_1$-$C_5$alkyl.

Preferably, $R_1$ and $R_2$ are the same or different and are selected from the group consisting of $C_1$-$C_3$ alkyl, phenyl, methylphenyl. More preferably, $R_1$ and $R_2$ are methyl.

Preferably, $R_3$ is selected from the group consisting of $CH_2R_8$, $CH_2CH_2R_8$, $CH=CHR_8$, $CH_2CH_2CH_2R_8$, $CH_2CH=CHR_8$, $CH=CHCH_2R_8$,

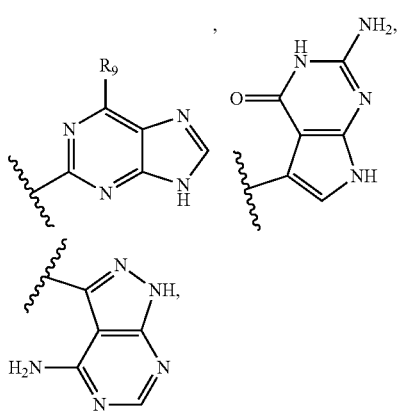

substituted or unsubstituted phenyl, benzyl, pyridyl, wherein the substituent or substituents are selected from the group consisting of methyl, F, Cl, Br, I, $NO_2$, CN, $NH_2$, $OCH_2X$, $CH_2X$, $CX_3$, $CH_2CH_2X$, OH, wherein X is selected from the group consisting of H, F, Cl, Br, I. More preferably, $R_3$ is selected from the group consisting of $CH=CHR_8$, $CH_2CH_2CH_2R_8$,

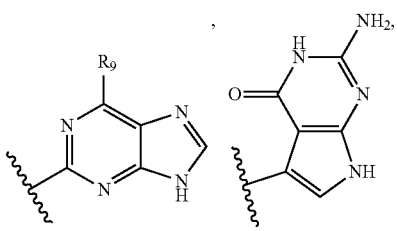
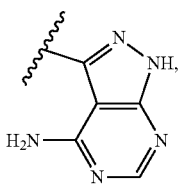

substituted or unsubstituted phenyl, pyridyl, wherein the substituent or substituents are selected from the group consisting of F, Cl, $NO_2$.

Preferably, $R_4$, $R_5$, $R_6$, $R_7$ are the same or different and they are selected from the group consisting of H, Cl, Br, I, $NH_2$, $OCH_3$. More preferably, $R_4$ and $R_7$ are H, $R_5$ and $R_6$ are $OCH_3$.

Preferably, $R_8$ is selected from the group consisting of

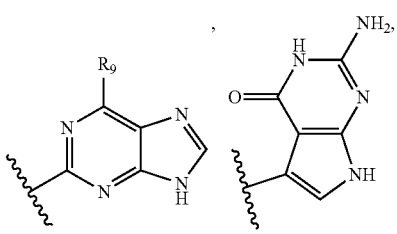
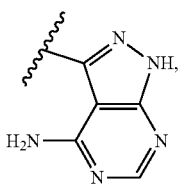

substituted or unsubstituted phenyl, benzyl, pyridyl, wherein the substituent or substituents are selected from the group consisting of methyl, F, Cl, Br, I, $NO_2$, CN, $NH_2$, $OCH_2X$, $CH_2X$, $CX_3$, $CH_2CH_2X$, OH, wherein X is selected from the group consisting of H, F, Cl, Br, I. More preferably, $R_8$ is selected from the group consisting of

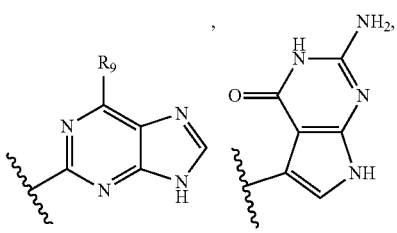

-continued

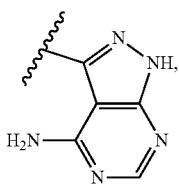

substituted or unsubstituted phenyl, pyridyl, wherein the substituent or substituents are selected from the group consisting of F, Cl, $NO_2$.

Preferably, $R_{10}$ is selected from the group consisting of $C_1$-$C_3$ alkyl, phenyl. More preferably, $R_{10}$ is methyl.

Preferably, $R_{11}$ and $R_{12}$ are the same or different and they are $C_1$-$C_3$ alkyl. More preferably, $R_{11}$ and $R_{12}$ are methyl.

The compounds of formula (I) contain at least one basic group and consequently they can form pharmaceutically acceptable salts through treatment with a suitable acid. Suitable acids include pharmaceutically acceptable organic acids as well as pharmaceutically acceptable inorganic acids. Examples of pharmaceutically acceptable salts include chloride, bromide, sulphate, phosphate, nitrate, acetate, propionate, butyrate, maleate, tartarate, citrate, lactate, oxalate, succinate and benzoate.

The compounds of formula (I) or their pharmaceutically acceptable salts can be used in the treatment of different types of malignant neoplasms (solid tumors, lymphomas and leukemia). Preferably, they are used in the treatment of ovarian cancer, breast cancer, prostate cancer, lung cancer and lymphomas. More preferably, they are used in the treatment of ovarian adenocarcinoma and small cell and non-small cell lung cancer.

The compounds of formula (I) or their pharmaceutically acceptable salts show powerful cytostatic and cytotoxic action and low acute and systemic toxicity.

The present invention provides also pharmaceutical compositions which comprise a compound of formula (I) or a pharmaceutically acceptable salt thereof. Such a pharmaceutical composition can be formulated so that it can be administrated through the appropriate route such as oral, intranasal, topical or parenteral administration. For example, such a pharmaceutical composition can be formulated into tablet, capsule, powder, solution, suspension, ointment or gel. Such a composition generally contains apart from a compound of formula (I) or a pharmaceutically acceptable salt thereof, a pharmaceutically acceptable carrier. Such a carrier may comprise excipients well known in the art, such as diluents, binders, fillers, disintegrants, lubricants, solvents, thickening agents, suspending agents, gelling agents, buffers or preservatives. These compositions can be prepared following methods which are well known in the art.

The present invention further provides a process for the preparation of compounds of formula (I) or their pharmaceutically acceptable salts.

A general route of synthesis of 1,2,4-triazolo-[3,4-b]-1,3,4-thiadiazole is presented below in Scheme 1.

Scheme 1

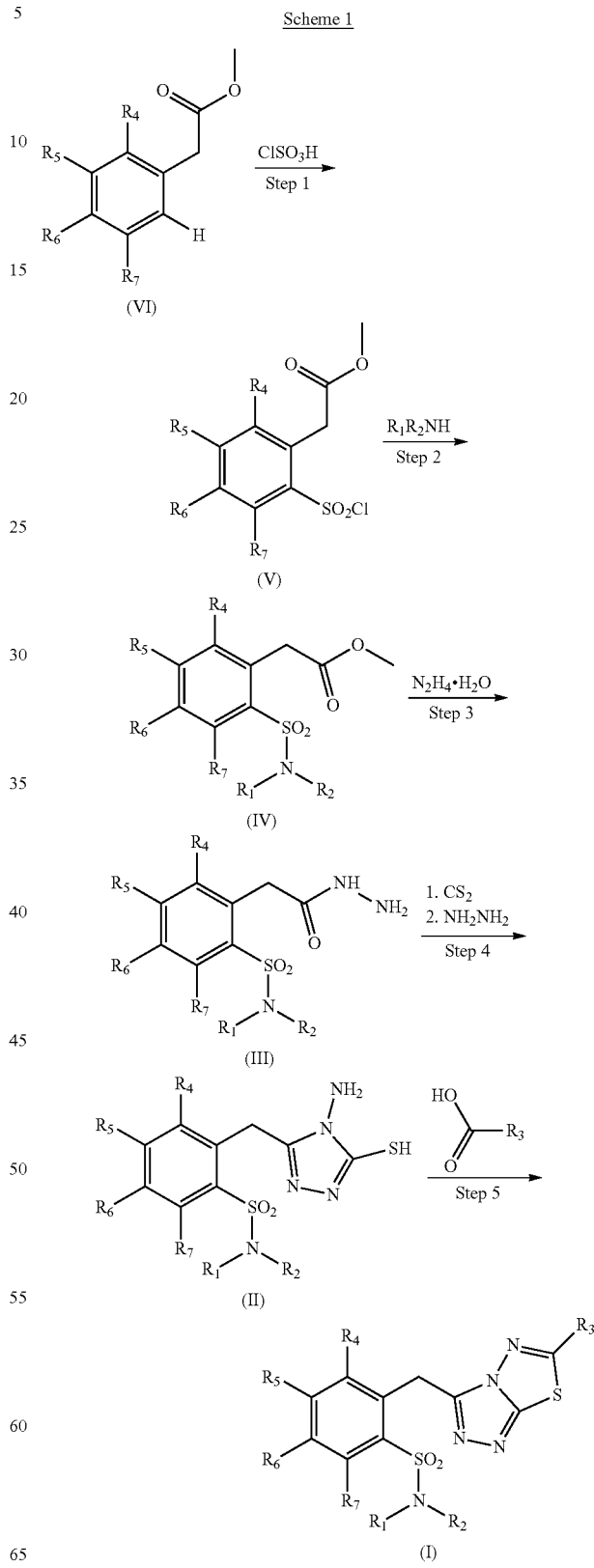

Sulfonyl chlorides (V) can be synthesized from the reaction of aromatic esters (VI) with chlorosulfonic acid. Sulfonamides (IV) can be produced though the reaction of sulfonyl chlorides (V) with amines. Hydrazides (III) can be prepared from sulfonamides (IV) with the treatment with aqueous hydrazine according to the methodology of Camoutsis and his colleagues (Ezabadi I R, Camoutsis C, Zoumpoulakis P, Geronikaki A, Soković M, Glamocilija J, Ciric A. Bioorg Med Chem. 2008, 16(3):1150-61). Steps 4 and 5 can be performed according to the method of Mathew and his colleagues (Mathew, V.; Keshavayya, J; Vaidya, V. P.; Giles, D. Eur. J. Med. Chem., 2007, 42, 521). Thus, hydrazides (III) can react with carbon disulfide and hydrazine, producing the amino triazoles (II) via the intermediates potassium salts of dithiocarbamates. Finally, amino triazoles (II) can be converted into 3,6-disubstitued 1,2,4-triazolo[3,4-b]-1,2,4 thiazoles (I) reacting with acids in the presence of phosphorus oxychloride.

EXAMPLE 1

Synthesis of 2-(2(chlorosulfonyl)-4,5-di methoxyphenyl)methyl acetate

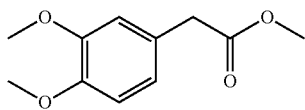

In a flask containing 2-(3,4-dimethoxyphenyl)methyl acetate (3.7 g, 17.65 mmol), CHCl$_3$ (35 ml) is added and then chlorosulfonic acid (5.28 ml, 79.4 mmol) dropwise at 0° C. under an Ar atmosphere. The solution obtains a dark purple color and is stirred at room temperature for 4 h. The reaction is quenched by the gradual addition of water (35 ml) at 0° C., followed by extractions with DCM (3×35 ml), drying the organic layer with Na$_2$SO$_4$, condensation and column chromatography with 2: 1 elution solvent PS/EA. The product is collected as a white solid in 88% yield.

Synthesis of 2-(N,N-dimethylsulfamoyl)-4,5-dimethoxy-phenylacetyl hydrazide

In an autoclave system containing 2-(2-(chlorosulfonyl)-4,5-dimethoxyphenyl)methyl acetate (450mg, 1.46mmol) dissolved in THF (1.8m1), a solution of dimethylamine was added in THF 2M (1.47 mL, 2.92 mmol) at 0° C. The reaction is stirred at room temperature for 1 h and a pale yellow solid is observed. After the reaction is completed, the solution is decanted into a flask with the required amount of DCM, concentrated on a rotary evaporator and the product is collected as a pale yellow solid in 100% yield.

Synthesis of 5-[2-(N,N-dimethylsulfamoyl)-4,5-dimethoxy-benzyl]-4-amino-3-mercapto-1,2,4-triazole In a cold solution of 2-(N,N-dimethylosulfamoyl)-4,5-dimethoxy-phenylacetyl hydrazide (0.01 mol), in absolute ethanol (150 mL), potassium hydroxide (0.015 mol) and carbon disulfide (0.015 mol) are added. The reaction mixture is stirred at room temperature for 20h. During the reaction, the intermediate potassium salt of dithiocarbamate precipitates. Subsequently, dry ether (150 mL) is added in order to complete the crystallization of the formed salt, which is obtained by filtration and further dryed with dry ether.

The salt as suspension in 80% aqueous hydrazine (0.02 mol), is stirred while heated under reflux for 2 h. The reaction mixture is cooled, dissolved in cold water and neutralized with 10% hydrochloric acid. The precipitate is collected by filtration, washed with cold water, dried and recrystallized in methanol.

Yield: 56%, M.p. 222-223° C. (CH$_3$OH), $^1$H NMR (500 MHz, DMSO-d6) δ 13.30 (s, 1H), 7.15 (s, 1H), 6.92 (s, 1H), 5.46 (s, 2H), 4.20 (s, 2H), 3.71 (s, 3H), 3.68 (s, 3H), 3.22 (s, 6H), $^{13}$C NMR (126 MHz, DMSO-d6) δ 165.8, 151.8, 151.5, 147.1, 127.7, 126.3, 115.6, 112.7, 55.9, 36.8, 28.1. Analysis: C$_{13}$H$_{19}$N$_5$O$_4$S$_2$ (373). Calc. %: C:41.82, H:5.09, N:18.76 Found: C:41.77, H:5.12, N:18.79

Synthesis of 3-[2-(N,N-dimethylsulfamoyl)-4,5-dimethoxy-benzyl]-6-phenyl-1,2,4-triazolo[3,4-b]-1,3,4-thiazole The mixture of 5[-2-(N,N-dimethylsulfamoyl)-4,5-dimethoxy-benzyl]-4-amino-3-mercapto-1,2,4-triazole (0.01 mol) and benzoic acid (0.01 mol) in dry phosphorous oxychloride (3.7 mL) is stirred while heated under reflux for 2 h. The reaction mixture is cooled to room temperature and then poured into ice. The excess of phosphorus oxychloride is neutralized with dry potassium carbonate and appropriate amount of potassium hydroxide until the pH of the reaction is above 8. The solid is filtered off, washed extensively with water and dried.

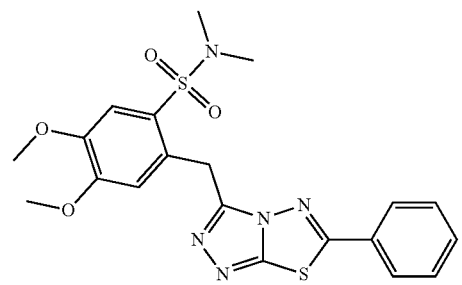 [SMILES: COc1cc(Cc2nnc3sc(-c4ccccc4)nn23)c(S(=O)(=O)N(C)C)cc1OC]

Yield: 74%, M.p. 212-214° C. (CH$_3$OH), $^1$H-NMR (CDCl$_3$) δ 7.95 (d, J=6.9 Hz, 2H), 7.68 (m, 1 H), 7.63 (m, 2H), 7.30 (s, 1 H), 7.21 (s, 1 H), 4.78 (s, 2H), 3.84 (s, 3H), 3.80 (s, 3H), 2.63 (s, 6H), I.R. ν cm$^{-1}$ 1601 (C═N), 1573, 1513, 1470, 1446 (C═C), 1265 (N—N═C), 1328 (S—O antisym.), 1141 (S—O sym.), Analysis: C$_{20}$H$_{21}$N$_5$O$_4$S$_2$ (459). Calc. %: C:52.28, H:4.57, N:15.25 Found: C:52.25, H:4.53, N:15.27

EXAMPLE 2

According to the methodology of example 1, the synthesis of the following thiazoles has been completed.

3-[2-(N,N-dimethylsulfamoyl)-4,5-dimethoxybenzyl]-6-(4-chlorophenyl)-1,2,4-triazolo[3,4-b]-1,3,4-thiazole

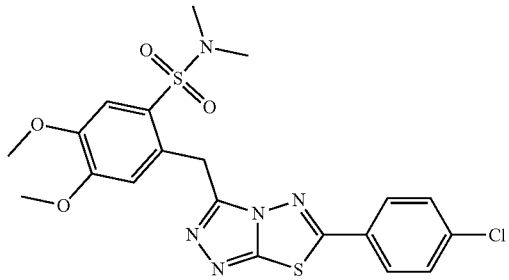 [SMILES: COc1cc(Cc2nnc3sc(-c4ccc(Cl)cc4)nn23)c(S(=O)(=O)N(C)C)cc1OC]

Yield: 52%. M.p. 228-229° C. (CH₃OH—CH₂Cl₂), ¹H-NMR (CDCl₃) δ 7.97 (d, J=8.5 Hz, 2H), 7.71 (d, J=8.6 Hz, 2H), 7.30 (s, 1H), 7.20 (s, 1H), 4.78 (s, 2H), 3.84 (s, 3H), 3.79 (s, 3H), 2.62 (s, 6H), I.R. ν cm⁻¹ 1600(C=N), 1573, 1519, 1470 (C=C), 1272 (N—N=C), 1339(S—O antisym.), 1138 (S—O sym), Analysis: $C_{20}H_{20}N_5O_4S_2Cl$ (493.5). Calc. %: C:48.63, H:4.05, N:14.18 Found: C:48.65, H:4.01, N:14.21.

3-[2-(N,N-dimethylsulfamoyl)-4,5-dimethoxybenzyl]-6-(3-methyl-4-nitrophenyl)-1,2,4-triazolo[3,4-b]-1,3,4-thiazole

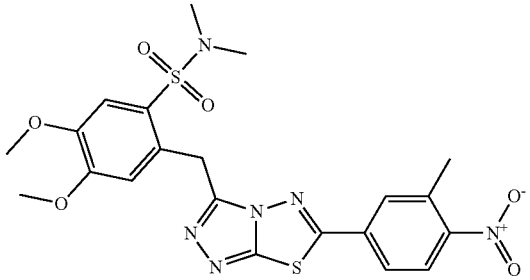 [SMILES: COc1cc(Cc2nnc3sc(-c4ccc([N+](=O)[O-])c(C)c4)nn23)c(S(=O)(=O)N(C)C)cc1OC]

Yield: 46%. M.p. 142-144° C. (CH₃OH), ¹H-NMR (CDCl₃) δ 8.18 (d, J=8.5 Hz, 1H), 8.08 (s, 1H), 8.02 (d, J=8.5 Hz, 1H), 7.30 (s, 1H), 7.22 (s, 1H), 4.80 (s, 2H), 3.84 (s, 3H), 3.80 (s, 3H), 2.62 (s, 6H), I.R. ν cm⁻¹ 1600(C=N), 1573, 1510, 1476 (C=C), 1271 (N—N=C), 1344 (S—O antisym.), 1133 (S—O sym.), Analysis: $C_{21}H_{22}N_6O_6S_2$ (518). Calc. %: C:48.64, H:4.24, N:16.21. Found: C:48.68, H:4.21, N:16.25.

3-[2-(N,N-dimethylsulfamoyl)-4,5-dimethoxybenzyl]-6-(2-chloro-4-nitrophenyl)-1,2,4-triazolo[3,4-b]-1,3,4-thiazole

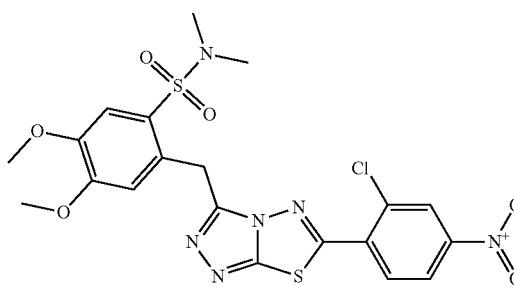

Yield: 65%. M.p. 216-217° C. (CH₃OH), ¹H-NMR (CDCl₃) δ 8.57 (d, J=2.3 Hz, 1H), 8.40 (dd, J=8.7, 2.3 Hz, 1H), 8.27 (d, J=8.7 Hz, 1H), 7.30 (s, 1H), 7.20 (s, 1H), 4.80 (s, 2H), 3.84 (s, 3H), 3.80 (s, 3H), 2.61 (s, 6H), I.R. ν cm⁻¹ 1603(C=N), 1573, 1518, 1476 (C=C), 1269 (N—N=C), 1331 (S—O antisym.), 1138 (S—O sym.), Analysis: $C_{20}H_{19}N_6O_6S_2Cl$ (538.5). Calc. %: C:44.56, H:3.52, N:15.60. Found: C:44.53, H:3.55, N:15.63.

3-[2-(N,N-dimethylsulfamoyl)-4,5-dimethoxybenzyl]-6-(3,4,5-trimethoxyphenyl)-1,2,4-triazolo[3,4-b]-1,3,4-thiazole

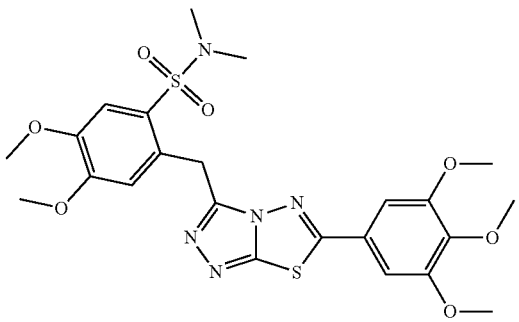

Yield: 38%. M.p. 169-170° C. (CH₃OH), ¹H-NMR (CDCl₃) δ 7.30 (s, 1H), 7.22 (s, 1H), 7.14 (s, 2H), 4.78 (s, 2H), 3.89 (s, 6H), 3.84 (s, 3H), 3.80 (s, 3H), 3.76 (s, 3H), 2.62 (s, 6H), I.R. ν cm⁻¹ 1630(C=N), 1586, 1459, 1414 (C=C), 1267 (N—N=C), 1333 (S—O antisym.), 1127 (S—O sym.), Analysis: $C_{23}H_{27}N_5O_7S_2$ (549). Calc. %: C:50.27, H:4.92, N:12.75. Found: C:50.25, H:4.96, N:12.78.

3-[2-(N,N-dimethylosulfamoyl)-4,5-dimethoxybenzyl]-6-(2-aminophenyl)-1,2,4-triazolo[3,4-b]-1,3,4-thiazole

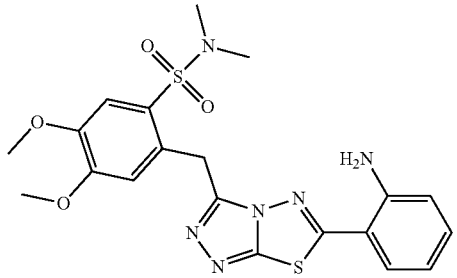 [SMILES: COc1cc(Cc2nnc3sc(-c4ccccc4N)nn23)c(S(=O)(=O)N(C)C)cc1OC]

Yield: 36%. M.p. 219-220° C. (C$_2$H$_5$OH), $^1$H-NMR (CDCl$_3$) δ 7.30 (s, 1H), 7.23 (t, J=7.8 Hz, 1H), 7.20 (s, 1H), 7.13 (m, 1H), 7.03 (d, J=8.35 Hz, 1H), 6.82 (d, J=8.2 Hz, 1H), 4.75 (s, 2H), 3.84 (s, 3H), 3.79 (s, 3H), 2.61 (s, 6H), I.R. ν cm$^{-1}$ 2436, 3382, 3267 (N—H), 1608 (C=N), 1555, 1514, 1474 (C=C), 1265 (N—N=C), 1328 (S—O antisym.), 1141 (S—O sym.), Analysis: C$_{20}$H$_{22}$N$_6$O$_4$S$_2$ (474). Calc. %: C:50.63, H:4.64, N:17.72. Found: C:50.60, H:4.61, N:17.75.

3-[2-(N,N-dimethylsulfamoyl)-4,5-dimethoxybenzyl]-6-(3-aminophenyl)-1,2,4-triazolo[3,4-b]-1,3,4-thiazole

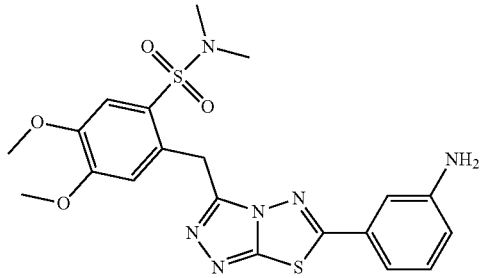 [SMILES: COc1cc(Cc2nnc3sc(-c4cccc(N)c4)nn23)c(S(=O)(=O)N(C)C)cc1OC]

Yield: 20%. M.p. 164-165° C. (C$_2$H$_5$OH), $^1$H-NMR (CDCl$_3$) δ 7.44 (dd, J=8.0, 1.4 Hz, 1H), 7.29 (m, 1H), 7.28 (s, 1H), 7.16 (s, 1H), 6.93 (d, J=8.4 Hz, 1H), 6.71 (bs, 2H, NH2), 6.68 (t, J=7.5 Hz, 1H), 4.81 (s, 2H), 3.84 (s, 3H), 3.78 (s, 3H), 2.63 (s, 6H), I.R. ν cm$^{-1}$, 3450, 3347 (N—H), 1626 (C=N), 1579, 1512, 1473 (C=C), 1272 (N—N=C), 1322 (S—O antisym.), 1129 (S—O sym.), Analysis: C$_{20}$H$_{26}$N$_6$O$_4$S$_2$ (474). Calc. %: C:50.63, H:4.64, N:17.72. Found: C:50.65, H:4.67, N:17.69.

3-[2-(N,N-dimethylsulfamoyl)-4,5-dimethoxybenzyl]-6-(4-aminophenyl)-1,2,4-triazolo[3,4-b]-1,3,4-thiazole

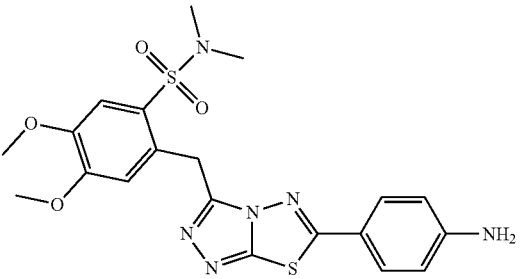 [SMILES: COc1cc(Cc2nnc3sc(-c4ccc(N)cc4)nn23)c(S(=O)(=O)N(C)C)cc1OC]

Yield: 18%. M.p. 179-181° C. (C$_2$H$_5$OH), $^1$H-NMR (CDCl$_3$) δ 7.58 (dd, J=8.6, 2.9 Hz, 2H), 7.29 (d, J=3.0 Hz, 1H), 7.19 (d, J=2.8 Hz, 1H), 6.68 (dd, J=8.6, 2.9 Hz, 2H), 6.17 (s, 2H), 4.72 (s, 2H), 3.84 (s, 3H), 3.78 (s, 3H), 2.61 (s, 6H), I.R. ν cm$^{-1}$ 3457, 3348, 3237 (N—H), 1603 (C=N), 1577, 1518, 1461 (C=C), 1265 (N—N=C), 1331 (S—O antisym.), 1138 (S—O sym.), Analysis: C$_{20}$H$_{26}$N$_6$O$_4$S$_2$ (474). Calc. %: C:50.63, H:4.64, N:17.72. Found: C:50.60, H:4.59, N:17.70.

3-[2-(N,N-dimethylsulfamoyl)-4,5-dimethoxybenzyl]-6-benzyl-1,2,4-triazolo[3,4-b]-1,3,4-thiazole Yield: 18%. M.p. 178-179° C. (CH$_3$OH); $^1$H-NMR (CDCl$_3$) δ 7.42-7.36 (m, 4H), 7.36-7.30 (m, 1H), 7.28 (s, 1H), 7.13 (s, 1H), 4.69 (s, 2H), 4.44, (s, 2H), 3.84 (s, 3H), 3.76 (s, 3H), 2.57 (s, 6H), I.R. ν cm$^{-1}$ 1601 (C=N), 1565, 1517, 1475 (C=C), 1267 (N—N=C), 1339 (S—O antisym.), 1140 (S—O sym.), Analysis: C$_{21}$H$_{23}$N$_5$O$_4$S$_2$ (473). Calc. %: C:53.27, H:4.86, N:14.80. Found: C:53.23, H:4.89, N:14.83.

3-[2-(N,N-dimethylsulfamoyl)-4,5-dimethoxybenzyl]-6-(3-methoxybenzyl)-1,2,4-triazolo[3,4-b]-1,3,4-thiazole

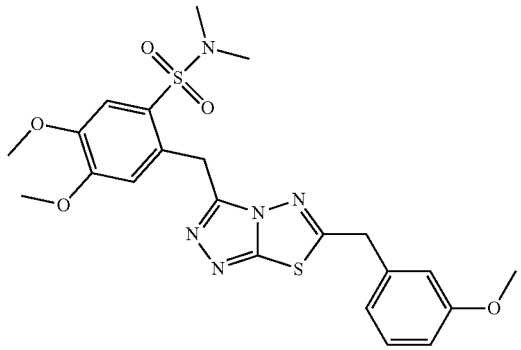

Yield: 58%. M.p. 165-166° C. (CH$_3$OH), $^1$H-NMR (CDCl$_3$) δ 7.30 (d, J=8.0 Hz, 1H), 7.29 (s, 1H), 7.13 (s, 1H), 6.97 (s, 1H), 6.94 (d, J=7.7 Hz, 1H), 6.90 (dd, J=8.3, 2.5 Hz, 1H), 4.70 (s, 2H), 4.41 (s, 2H), 3.84 (s, 3H), 3.77 (s, 3H), 3.75 (s, 3H), 2.57 (s, 6H), I.R. ν cm$^{-1}$ 1607 (C=N), 1581, 1515, 1491 (C=C), 1266 (N—N=C), 1334 (S—O antisym.), 1139 (S—O sym.), Analysis: C$_{22}$H$_{25}$N$_5$O$_5$S$_2$ (503). Calc. %: C:52.48, H:4.97, N:13.91. Found: C:52.44, H:4.95, N:12.88.

3-[2-(N,N-dimethylsulfamoyl)-4,5-dimethoxybenzyl]-6-(4-methoxybenzyl)-1,2,4-triazolo[3,4-b]-1,3,4-thiazole

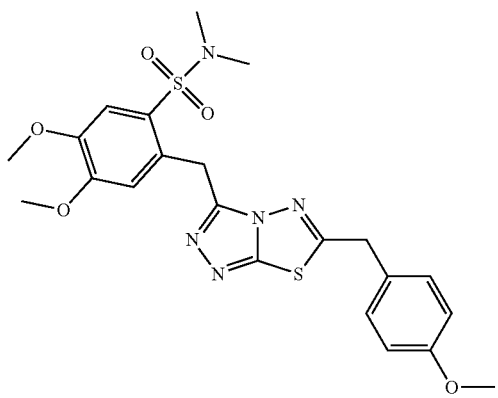

Yield: 52%. M.p. 184-185° C. (CH$_3$OH), $^1$H-NMR (CDCl$_3$) δ 7.30 (d, J=8.6 Hz, 2H), 7.29 (s, 1H), 7.13 (s, 1H), 6.94 (d, J=8.6 Hz, 2H), 4.69 (s, 2H), 4.36 (s, 2H), 3.84 (s, 3H), 3.77 (s, 3H), 3.75 (s, 3H), 2.57 (s, 6H), I.R. ν cm$^{-1}$ 1610 (C=N), 1571, 1514, 1476 (C=C), 1267 (N—N=C), 1340 (S—O antisym.), 1140 (S—O sym.), Analysis: C$_{22}$H$_{25}$N$_5$O$_5$S$_2$ (503). Calc. %: C:52.48, H:4.97, N:13.91. Found: C:52.45, H:4.99, N:13.94.

3-[2-(N,N-dimethylsulfamoyl)-4,5-dimethoxybenzyl]-6-(3,4-dimethoxybenzyl)-1,2,4-triazolo[3,4-b]-1,3,4-thiazole

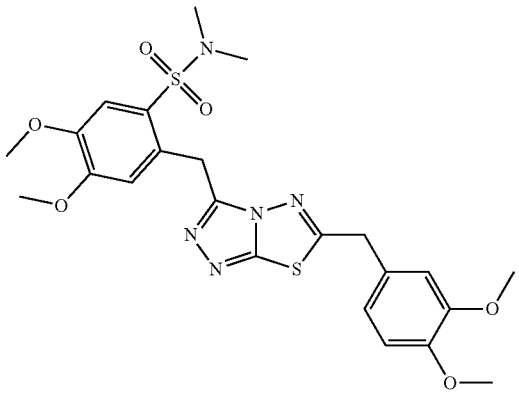

Yield: 50%. M.p. 139-140° C. (CH$_3$OH), $^1$H-NMR (CDCl$_3$) δ 7.29 (s, 1 H), 7.13 (s, 1 H), 6.99 (s, 1 H), 6.95 (d, J=8.2 Hz, 1 H), 6.90 (dd, J=8.3, 2.0 Hz, 1H), 4.70 (s, 2H), 4.35 (s, 2H), 3.84 (s, 3H), 3.77 (s, 3H), 3.75 (s, 3H), 3.73 (s, 3H), 2.58 (s, 6H), I.R. ν cm$^{-1}$ 1602 (C=N), 1555, 1516, 1462 (C=C), 1266 (N—N=C), 1336 (S—O antisym.), 1139 (S—O sym.), Analysis: C$_{23}$H$_{27}$N$_5$O$_6$S$_2$ (533). Calc. %: C:51.78, H:5.06, N:13.13. Found %: 0:51.81, H:5.10, N:13.15.

3-[2-(N,N-dimethylsulfamoyl)-4,5-dimethoxybenzyl]-6-(3-phenylpropyl)-1,2,4-triazolo[3,4-b]-1,3,4-thiazole

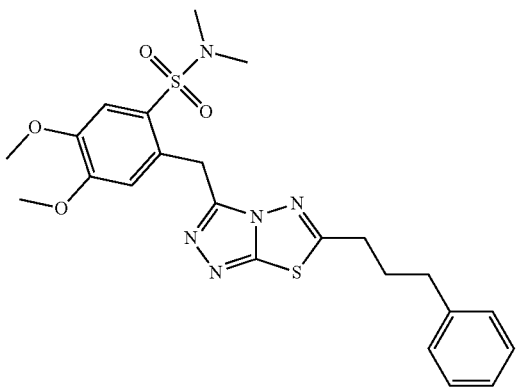 [SMILES: COc1cc(Cc2nnc3sc(CCCc4ccccc4)nn23)c(S(=O)(=O)N(C)C)cc1OC]

Yield: 14%. M.p. 128-129° C. (CH$_3$OH), $^1$H-NMR (CDCl$_3$) δ 7.30-7.26 (m, 3H), 7.23-7.17 (m, 3H), 7.12 (s, 1H), 4.69 (s, 2H), 3.82 (s, 3H), 3.77 (s, 3H), 3.04 (t, J=7.4 Hz, 2H), 2.68 (t, J=7.7 Hz, 2H), 2.59 (s, 6H), 2.03 (p, J=7.6 Hz, 2H), I.R. ν cm$^{-1}$ 1600 (C=N), 1574, 1516, 1478 (C=C), 1267 (N—N=C), 1334 (S—O antisym.), 1139 (S—O sym.), Analysis: C$_{23}$H$_{27}$N$_5$O$_4$S$_2$ (501). Calc. %: C:55.09, H:5.38, N:13.97. Found %: C:55.11, H:5.41, N:14.01.

3-[2-(N,N-dimethylsulfamoyl)-4,5-dimethoxybenzyl]-6-(2-pyridinyl)-1,2,4-triazolo[3,4-b]-1,3,4-thiazole

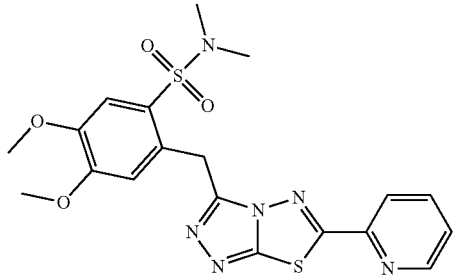 [SMILES: COc1cc(Cc2nnc3sc(-c4ccccn4)nn23)c(S(=O)(=O)N(C)C)cc1OC]

Yield: 32%. M.p. 198-199° C. (CH$_3$OH), $^1$H-NMR (CDCl$_3$) δ 8.76, (s, 1H), 8.23-8.00 (m, 2H), 7.69 (s, 1H), 7.37-7.15 (m, 2H), 4.79 (s, 2H), 3.83 (s, 3H), 3.78 (s, 3H), 2.62 (s, 6H), I.R. ν cm$^{-1}$ 1599 (C=N), 1576, 1517, 1456 (C=C), 1270 (N—N=C), 1335 (S—O antisym.), 1137 (S—O sym.), Analysis: C$_{19}$H$_{20}$N$_6$O$_4$S$_2$ (460). Calc. %: C:49.56, H:4.34, N:18.26. Found %: C:49.60, H:4.31, N:18.30.

3-[2-(N,N-dimethylsulfamoyl)-4,5-dimethoxybenzyl]-6-(4-pyridinyl)-1,2,4-triazolo[3,4-b]-1,3,4-thiazole

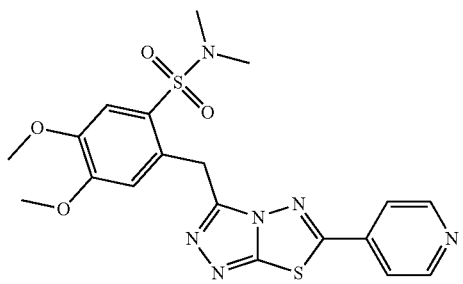 [SMILES: COc1cc(Cc2nnc3sc(-c4ccncc4)nn23)c(S(=O)(=O)N(C)C)cc1OC]

Yield: 37%. M.p. 231-232° C. (C$_2$H$_5$OH), $^1$H-NMR (CDCl$_3$) δ 8.85 (d, J=5.0 Hz, 2H), 7.91 (d, J=5.0 Hz, 2H), 7.30 (s, 1H), 7.21 (s, 1H), 4.80 (s, 2H), 3.84 (s, 3H), 3.80 (s, 3H), 2.63 (s, 6H), I.R. ν cm$^{-1}$ 1600 (C=N), 1561, 1507, 1473, 1411 (C=C), 1274 (N—N=C), 1337 (S—O antisym.), 1138 (S—O sym.), Analysis: C$_{19}$H$_{20}$N$_6$O$_4$S$_2$ (460). Calc. %: C:49.56, H:4.34, N:18.26. Found %: C:49.58, H:4.37, N:18.23.

3-[2-(N,N-dimethylsulfamoyl)-4,5-dimethoxybenzyl]-6-(3-bromo-5-pyridinyl)-1,2,4-triazolo[3,4-b]-1,3,4-thiazole

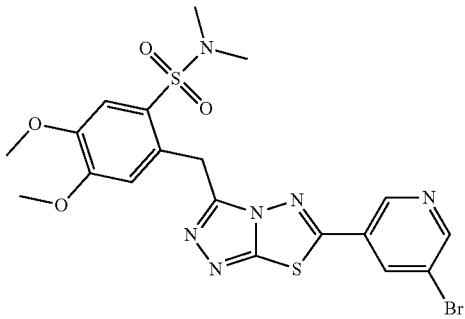 [SMILES: COc1cc(Cc2nnc3sc(-c4cncc(Br)c4)nn23)c(S(=O)(=O)N(C)C)cc1OC]

Yield: 41%. M.p. 227-228° C. (C$_2$H$_5$OH), $^1$H-NMR (CDCl$_3$) δ 9.10 (d, J=2.0 Hz, 1H), 8.98 (d, J=2.2 Hz, 1H), 8.58 (s, 1H), 7.30 (s, 1H), 7.22 (s, 1H), 4.79 (s, 2H), 3.84 (s, 3H), 3.80 (s, 3H), 2.63 (s, 6H), I.R. ν cm$^{-1}$ 1600 (C=N), 1573, 1516, 1481, 1440, 1412 (C=C), 1270 (N—N=C), 1338 (S—O antisym.), 1140 (S—O sym.), Analysis: C$_{19}$H$_{19}$BrN$_6$O$_4$S$_2$ (539). Calc. %: C:42.30, H:3.52, N:15.58. Found %: C:42.32, H:3.49, N:15.56.

3-[2-(N,N-dimethylsulfamoyl)-4,5-dimethoxybenzyl]-6-cinnamyl-1,2,4-triazolo[3,4-b]-1,3,4-thiazole

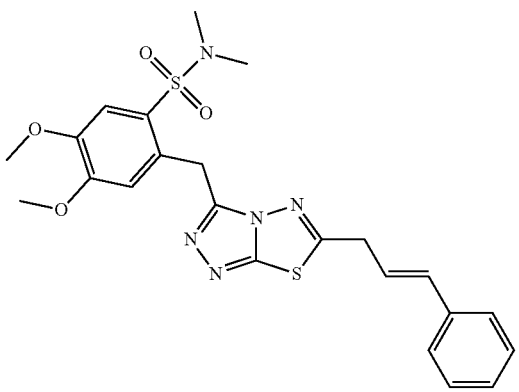 [SMILES: COc1cc(Cc2nnc3sc(C/C=C/c4ccccc4)nn23)c(S(=O)(=O)N(C)C)cc1OC]

Yield: 44%. M.p. 191-193° C. (CH$_3$OH—CH$_2$Cl$_2$); $^1$H-NMR (CDCl$_3$) δ 7.81 (d, J=7.1 Hz, 2H), 7.64 (d, J=16.4 Hz, 1H), 7.60 (d, J=16.3 Hz, 1H), 7.52-7.40 (m, 3H), 7.30 (s, 1H), 7.16 (s, 1H), 4.73 (s, 2H), 3.84 (s, 3H), 3.80 (s, 3H), 2.62 (s, 6H), I.R. ν cm$^{-1}$ 1630 (CH=CH), 1600 (C=N), 1575, 1576, 1475 (C=C), 1267 (N—N=C), 1332 (S—O antisym.), 1138 (S—O sym.), Analysis: C$_{22}$H$_{23}$N$_5$O$_4$S$_2$ (485). Calc. %: C:54.43, H:4.74, N:14.43. Found %: C:54.45, H:4.71, N:14.39.

3-[2-(N,N-dimethylsulfamoyl)-4,5-dimethoxybenzyl]-6-(E)-4-fluorostyryl-1,2,4-triazolo[3,4-b]-1,3,4-thiazole

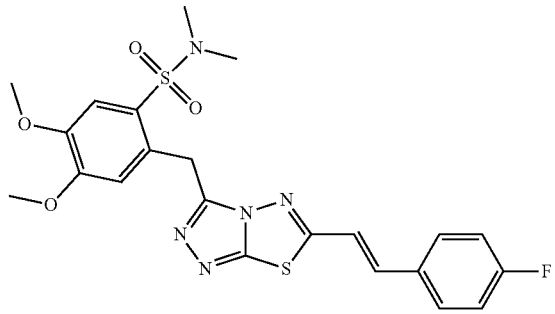 [SMILES: COc1cc(Cc2nnc3sc(/C=C/c4ccc(F)cc4)nn23)c(S(=O)(=O)N(C)C)cc1OC]

Yield: 73%. M.p. 210-212° C. $^1$H NMR (500 MHz, DMSO-d6) δ 7.89 (dd, J=8.6, 5.6 Hz, 2H), 7.65 (d, J=16.4 Hz, 1H), 7.58 (d, J=16.4 Hz, 1H), 7.36-7.25 (m, 2H), 7.16 (s, 1H), 4.72 (s, 2H), 3.84 (s, 3H), 3.79 (s, 3H), 2.60 (s, 6H). I.R. ν cm$^{-1}$ 2926, 2853, 1736, 1631, 1601, 1513, 1494, 1474, 1387, 1337, 1268, 1231, 1139, 1156, 1048.

3-[2-(N,N-dimethylsulfamoyl)-4,5-dimethoxybenzyl]-6-(E)-4-chlorostyryl-1,2,4-triazolo[3,4-b]-1,3,4-thiazole

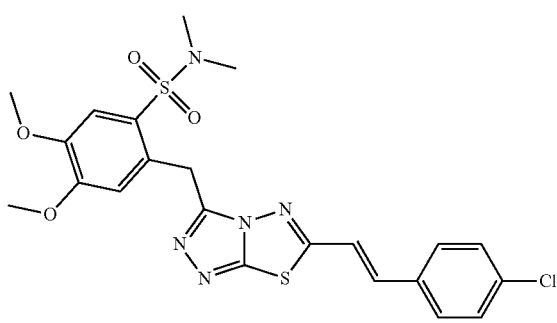 [SMILES: COc1cc(Cc2nnc3sc(/C=C/c4ccc(Cl)cc4)nn23)c(S(=O)(=O)N(C)C)cc1OC]

Yield: 72%. M.p. 229-231° C. $^1$H NMR (500 MHz, DMSO-d6) δ 7.84 (d, J=8.6 Hz, 2H), 7.64 (s, 2H), 7.53 (d, J=8.6 Hz, 2H), 7.30 (s, 1H), 7.15 (s, 1H), 4.72 (s, 2H), 3.84 (s, 3H), 3.79 (s, 3H), 2.61 (s, 6H). $^{13}$C NMR (126 MHz, DMSO-d6) δ 165.7, 151.9, 147.2, 146.3, 139.4, 134.8, 133.3, 129.8, 129.0, 127.9, 126.1, 119.0, 115.5, 112.7, 55.9, 36.8, 27.6. I.R. ν cm$^{-1}$ 2934, 2844, 1726, 1633, 1516, 1488, 1473, 1410, 1381, 1339, 1268, 1224, 1139, 1175, 1087.

3-[2-(N,N-dimethylsulfamoyl)-4,5dimethoxybenzyl]-6-(E)-3-fluorostyryl-1,2,4-triazolo[3,4-b]-1,3,4-thiazole

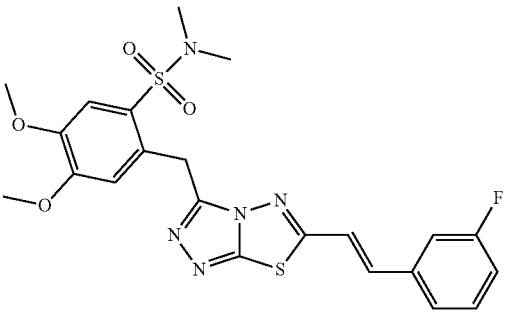 [SMILES: COc1cc(Cc2nnc3sc(/C=C/c4cccc(F)c4)nn23)c(S(=O)(=O)N(C)C)cc1OC]

Yield: 52%. M.p. 212-215° C. $^1$H NMR (500 MHz, DMSO-d6) δ 7.92-7.73 (m, 2H), 7.68 (td, J=8.1, 5.8 Hz, 1H), 7.55 (td, J=8.6, 2.4 Hz, 1H), 7.30 (s, 1H), 7.21 (s, 1H), 4.78 (s, 2H), 3.84 (s, 3H), 3.80 (s, 3H), 2.63 (s, 6H). I.R. ν cm$^{-1}$ 2929, 2844, 1589, 1516, 1474, 1387, 1338, 1270, 1228, 1174, 1155, 1140, 1042

3-[2-(N,N-dimethylsulfamoyl)-4,5-dimethoxybenzyl]-6-phenoxymethyl-1,2,4-triazolo[3,4-b]-1,3,4-thiazole

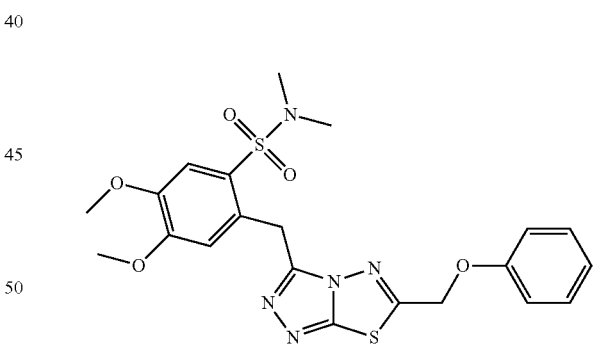

Yield: 41%. M.p. 178-179° C. (CH$_3$OH—CH$_2$Cl$_2$), $^1$H-NMR (CDCl$_3$) δ 7.37-7.31 (m, 2H), 7.29 (s, 1H), 7.13 (s, 1H), 7.09 (d, J=7.7, 1.0 Hz, 2H), 7.06-7.01 (m, 1H), 5.55 (s, 2H), 4.72 (s, 2H), 3.84 (s, 3H), 3.78 (s, 3H), 2.58 (s, 6H), I.R. ν cm$^{-1}$ 1598 (C=N), 1572, 1516, 1479 (C=C), 1267 (N—N=C), 1337 (S—O antisym.), 1139 (S—O sym.), Analysis: C$_{21}$H$_{23}$N$_5$O$_5$S$_2$ (489). Calc. %: C:51.53, H:4.70, N:14.31. Found %: C:51.51, H:4.67, N:14.33.

p 3-[2-(N,N-dimethylsulfamoyl)-4,5-dimethoxybenzyl]-6-[2-(2-methoxyphenyl) ethyl]-1,2,4-triazolo[3,4-b]-1,3,4-thiazole

3-[2-(N,N-dimethylsulfamoyl)-4,5-dimethoxybenzyl]-6-(3-chlorophenyl)-1,2,4-triazolo[3,4-b]-1,3,4-thiazole

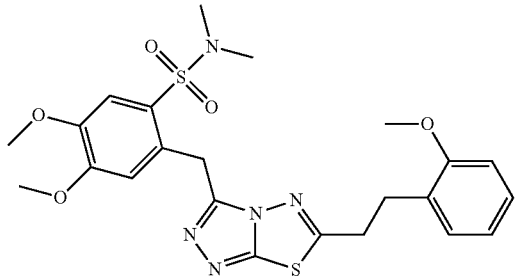 [SMILES: COc1ccccc1CCc1nn2c(Cc3cc(OC)c(OC)cc3S(=O)(=O)N(C)C)nnc2s1]
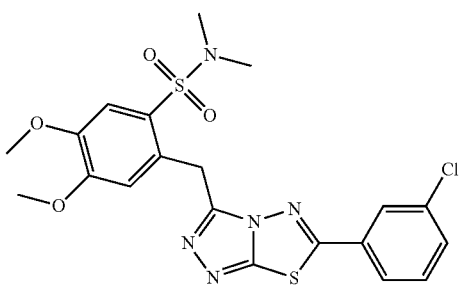 [SMILES: COc1cc(Cc2nnc3sc(-c4cccc(Cl)c4)nn23)c(S(=O)(=O)N(C)C)cc1OC]

Yield: 37%. M.p. 154-155° C. (CH$_3$OH—CH$_2$Cl$_2$), $^1$H-NMR (CDCl$_3$) δ 7.29 (s, 1H), 7.21 (m, 1H), 7.17 (d, J=7.5 Hz, 1H), 7.10 (s, 1H), 6.95 (d, J=8.2 Hz, 1H), 6.84 (t, J=7.26 Hz, 1H), 4.67 (s, 2H), 3.84 (s, 3H), 3.77 (s, 3H), 3.75 (s, 3H), 3.29 (m, 2H), 3.01 (t, J=7.5 Hz, 4H), 2,56 (s, 6H), I.R. v cm$^{-1}$ 1601 (C=N), 1569, 1519, 1477 (C=C), 1267 (N—N=C), 1336 (S—O antisym.), 1139 (S—O sym.), Analysis: C$_{23}$H$_{27}$N$_5$O$_5$S$_2$ (517). Calc. %: C:53.38, H:5.22, N:13.53. Found %: C:53.41, H:5.19, N:13.56.

Yield: 45%. M.p. 237-239° C., $^1$H NMR (500 MHz, CDCl$_3$) δ 7.86 (s, 1H), 7.74 (d, J=7.7 Hz, 1H), 7.56 (d, J=8.0 Hz, 1 H), 7.53-7.39 (m, 2H), 6.99 (s, 1 H), 4.90 (s, 2H), 3.93 (s, 3H), 3.87 (s, 3H), 2.72 (s, 6H). $^{13}$C NMR (126 MHz, CDCl$_3$) δ 164.9, 153.1, 152.5, 147.7, 146.8, 135.7, 132.7, 130.9, 130.8, 127.9, 127.03, 127.0 125.3, 114.4, 113.4, 56.4, 56.2, 36.9, 27.9. I.R. v cm$^{-1}$ 3088, 3056, 2955, 2927, 2852, 2616, 1598, 1573, 1518, 1482, 1470, 1439, 1405, 187, 1339, 1270, 1228, 1175, 1139, 1101, 1078, 1043.

3-[2-(N,N-dimethylsulfamoyl)-4,5-dimethoxybenzyl]-6-[2-(4-methoxyphenyl) ethyl]-1,2,4-triazolo[3,4-b]-1,3,4-thiazole

3-[2-(N,N-dimethylsulfamoyl)-4,5-dimethoxybenzyl]-6-(4-nitrophenyl)-1,2,4-triazolo[3,4-b]-1,3,4-thiazole

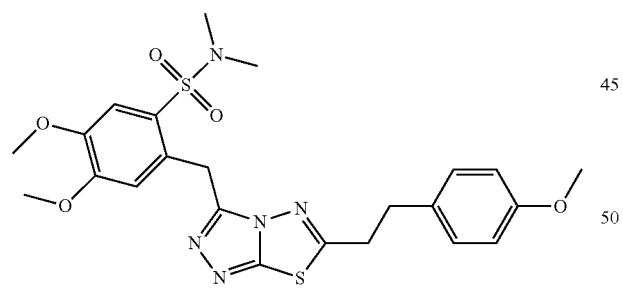

Yield: 41%. M.p. 151-152° C. (CH$_3$OH—CH$_2$Cl$_2$), $^1$H-NMR (CDCl$_3$) δ 7.29 (s, 1H), 7.18 (d, J=8.3 Hz, 2H), 7.11 (s, 1 H), 6.83 (d, J=8.1 Hz, 2H), 4.67 (s, 2H), 3.83 (s, 3H), 3.77 (s, 3H), 3.71 (s, 3H), 2.99 (t, J=7.6 Hz, 2H), 2.55 (s, 6H), I.R. v cm$^{-1}$ 1601 (C=N), 1569, 1519, 1477 (C=C), 1267 (N—N=C), 1336 (S—O antisym.), 1139 (S—O sym.), Analysis: C$_{23}$H$_{27}$N$_5$O$_5$S$_2$ (517). Calc. %: C:53.38, H:5.22, N:13.53. Found %: C: 53.35, H:5.24, N:13.50.

Yield: 53%. M.p. 223-225° C., $^1$H NMR (500 MHz, CDCl$_3$) δ 8.39 (d, J=8.7 Hz, 2H), 8.08 (d, J=8.7 Hz, 2H), 7.45 (s, 1H), 7.00 (s, 1H), 4.94 (s, 2H), 3.93 (s, 3H), 3.88 (s, 3H), 2.73 (s, 6H), $^{13}$C NMR (126 MHz, CDCl$_3$) δ 163.9, 153.1, 152.5, 150.1, 147.9, 147.1, 134.8, 128.2, 127.5, 126.9, 124.7, 114.5, 113.1, 113.1, 56.4, 37.1, 28.0, I.R. v cm$^{-1}$ 3108, 3004, 2931, 2837, 1600, 1534, 1571, 1518, 1471, 1351, 1337, 1270, 1227, 1138, 1049

3-[2-(N,N-dimethylsulfamoyl)-4,5-dimethoxybenzyl]-6-(4-fluorophenyl)-1,2,4-triazolo[3,4-b]-1,3,4-thiazole

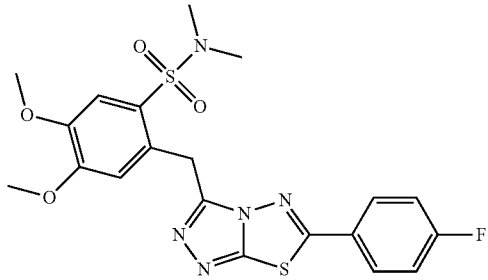 [SMILES: COc1cc(Cc2nnc3sc(-c4ccc(F)cc4)nn23)c(S(=O)(=O)N(C)C)cc1OC]

Yield: 66%. M.p. 220-223° C., $^1$H NMR (500 MHz, DMSO-d6) δ 8.02 (dd, J=8.8, 5.2 Hz, 2H), 7.48 (t, J=8.8 Hz, 2H), 7.30 (s, 1H), 7.20 (s, 1H), 4.78 (s, 2H), 3.84 (s, 3H), 3.79 (s, 3H), 2.62 (s, 6H), I.R. ν cm$^{-1}$ 2933, 2842, 1602, 1517, 1475, 187, 1337, 1268, 1241, 1225, 1139, 1042

3-[2-(N,N-dimethylsulfamoyl)-4,5-dimethoxybenzyl]-6-(2,4-dinitrophenyl)-1,2,4-triazolo[3,4-b]-1,3,4-thiazole

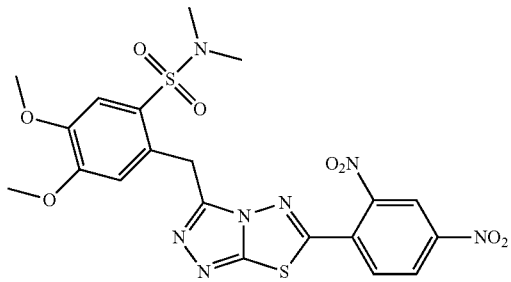 [SMILES: COc1cc(Cc2nnc3sc(-c4ccc([N+](=O)[O-])cc4[N+](=O)[O-])nn23)c(S(=O)(=O)N(C)C)cc1OC]

Yield: 29%. M.p. 162-164° C., $^1$H NMR (500 MHz, DMSO-d6) δ 8.74 (s, 1H), 8.69 (d, J=8.4 Hz, 1H), 8.50 (d, J=8.6 Hz, 1H), 7.29 (s, 1H), 7.13 (s, 1H), 4.74 (s, 2H), 3.83 (s, 3H), 3.79 (s, 3H), 2.58 (s, 6H), $^{13}$C NMR (126 MHz, DMSO-d6) δ 161.2, 153.8, 151.9, 150.5, 149.3, 147.3, 146.3, 128.2, 127.7, 127.6, 126.9, 126.1, 124.3, 115.4, 112.8, 55.9, 55.8, 36.7, 27.6, I.R. ν cm$^{-1}$ 2917, 2850, 1729, 1555, 1514, 1457, 1346, 1308, 1270, 1223, 1137, 1042

EXAMPLE 3

In vitro Study of Cytostatic-cytotoxic Activity Against Human Cancer and Leukemia Cell Lines The present example illustrates the cytostatic-cytotoxic effects of the following compounds of the present invention against the human ovarian cancer cell lines UWB1,289 (with mutant BRCA1), UWB1,289+BRCA1, OVCAR-3, SCOV-3, the human breast cancer cell lines MCF –7 [expressing estrogen receptors, insulin-like growth factor binding proteins (IGFBP) BP-2, BP-4; BP-5), oncogene WNT7B], T-47D (positive for the expression of all steroid receptors and the oncogene WNT7B), the human cancer cell line of hormone-resistant prostate cancer PC-3, the human acute T-leukemia cell line MOLT-4 (do not show expression of the mutant P53 oncogene), and the human lung carcinoma cell line A549 bearing a mutation in the KRAS oncogene (p.G12S c.34G>A).

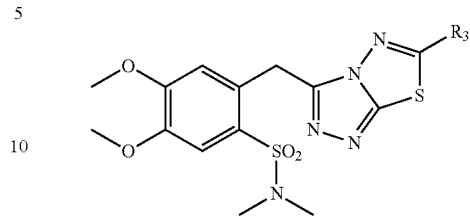

The R3 substituent of the compounds studied is defined in Table 1:

TABLE 1

| Ένωση | R$_3$ | Ένωση | R$_3$ |
|---|---|---|---|
| TS167 | C$_6$H$_5$— | TS50 | 4-CH$_3$O—C$_6$H$_4$CH$_2$— |
| TS63 | 4-Cl—C$_6$H$_4$— | TS51 | 3,4-CH$_3$O—C$_6$H$_3$CH$_2$— |
| TS57 | 2-NH$_2$—C$_6$H$_4$— | TS56 | C$_6$H$_5$—OCH$_2$— |
| TS70 | 3-NH$_2$—C$_6$H$_4$— | TS53 | C$_6$H$_5$—CH=CH— |
| TS71 | 4-NH$_2$—C$_6$H$_4$— | TS54 | 2-CH$_3$O—C$_6$H$_4$CH$_2$CH$_2$— |
| TS61 | 2-Cl-4-NO$_2$—C$_6$H$_3$— | TS55 | 4-CH$_3$O—C$_6$H$_4$CH$_2$CH$_2$— |
| TS60 | 2-CH$_3$-4-NO$_2$C$_6$H$_3$— | TS52 | C$_6$H$_5$CH$_2$CH$_2$CH$_2$— |
| TS59 | 3,4,5-CH$_3$O—C$_6$H$_2$— | TS66 | 2-pyridyl |
| TS62 | C$_6$H$_5$CH$_2$— | TS65 | 4-pyridyl |
| TS58 | 3-CH$_3$O—C$_6$H$_4$CH$_2$— | TS67 | 5-bromo-3-pyridyl |
| TS22 | 3-Cl—C$_6$H$_4$— | TS25 | 4-F—C$_6$H$_4$—CH=CH— |
| TS29 | 3-F—C$_6$H$_4$— | TS26 | 4-Cl—C$_6$H$_4$—CH=CH— |

Specific Characteristics of Ovarian Cancer Cell Lines

SKOV-3 (SKOV-3) (ATCC HTB 77) and OVCAR-3 (ATCC® HTB-161™)

Human ovarian adenocarcinoma cells, which are grown easily in monolayer culture with epithelial-like morphology. SKOV-3 are resistant to tumor necrosis factor (TNF) and to other cytotoxic drugs such as cisplatin, and adriamycin, while OVCAR-3 are resistant to adriamycin, cisplatin and melphalan. These cell lines express androgens, estrogens and progesterone receptors. When SKOV-3 or OVCAR-3 cells are subcutaneously implanted in nude mice, SCID mice, a moderately differentiated tumor develops, and the resulting model resembles primary ovarian adenocarcinoma in humans.

UWB1.289 (ATCC CRL-2945)

Human ovarian adenocarcinoma cells, which are grown easily in monolayer culture, have morphology of epithelial cancer cells and do not express estrogenic and progesterone receptors. Also, UWB1.289 cells have mutated the p53 tumor suppressor gene and positive Wilms' tumor protein (WT) expression, have no functional BRCA1 gene and are positive for the expression of cytokeratin 7 (CK-7), calretinin and Wilms' tumor protein (WT). Finally they are sensitive to ionizing radiation.

UBWB1.289+BRCA1 (ATCC CRL-2946)

Human ovarian adenocarcinoma cells, derived from UBWB1,289, in which the presence of the BRCA1 gene has been restored. They grow easily in culture, creating monolayers, have morphology of epithelial cancer cells and do not express estrogenic and progesterone receptors. They are not susceptible to ionizing radiation and radioimmune chemical agents (e.g., alkylating agents). Also, UWB1.289 cells have mutated the p53 tumor suppressor gene, and are positive for the expression of cytokeratin 7 (CK-7), calretinin and Wilms' tumor protein (WT).

Cell Culture

All cancer cell lines are stored in a liquid nitrogen tank in 2.5 ml cryovials (Corning-Costar, Cambridge, Mass.). DMSO (dimethylsulfoxide) act as a cryoprotectant and is added to prevent the formation of ice crystals which may lyse the cells. The Cells were grown as monolayer cultures in T-75 flasks (Corning-Costar, Cambridge, Mass.) and maintained at 37° C. in 5% $CO_2$ incubator & 100% relative humidity. The cultures medium used are McCoy's 5a Medium, supplemented with 10% fetal bovine serum (FBS, Gibco) and 1% antibiotics (100 IU/ml penicillin/100 pg/ml streptomycin), sterilized by filtration (Corning-Costar filter, diameter 0.2 μm, RPMI-1640 and 50% RPMI-1640 (Catalog No 30-2001) plus 50% Mammary Epithelial Growth Medium (MEGM), supplemented with 10% fetal bovine serum (FBS, Gibco) and 1% antibiotics (100 IU/ml penicillin/100 μg/ml streptomycin). The passage is performed every 3-4 to days as follows: Cells are washed with sterile PBS (Phosphate buffered saline): 8 g/l NaCl, 0,2 g/l KCl, 1,15 g/l $Na_2HPO4_{KCl}$ 0,2 g/l $KH_2PO4$. pH:7,4), add 2-3 ml 0.05% trypsin (Gibco 1:250) and 0.02% EDTA to cover the monolayer and incubate the flask at 3TC for 5-10 minutes. Trypsin-EDTA, is used mainly to detach the cells from the flask and prepare a single cell suspension. Finally, the number of cells can be determined by direct counting using a Neubauer chamber and cell viability is determined by staining the cells with trypan blue.

In Vitro Study

In the experimental study the in vitro effect of the compound type (I) was evaluated against ovarian cancer cell lines UWB1.289, UWB1.289+BRCA1 Kai SKOV-3.The cells were plated in 96-well plate (MTP) at a density of $1×10^4$ cells/ml per well and maintained for 72 h at 3TC in a 5% $CO_2$ incubator and grown as monolayers. The selection of the initial number of cells was made according to the rate of proliferation of the cell line, in order the cells throughout the experiment are in an exponential (log) growth phase. After 24 hours, cells were treated with 1-100 μmol/l of the tested compounds for 48 h. Experiments were carried out using triplicate wells. The viability of cultured cells was estimated by an (3-(4,5-imethylthiazol-2-yl)-2,5-diphenyltetrazolium bromide (MTT) metabolic assay as described previously (Finlay G J, Wilson W R and Baguley B C: Comparison of in vitro activity of cytotoxic drugs towards human carcinoma and leukaemia cell lines. Eur J Cancer Clin Oncol 22: 655-662, 1986; Alley M C, Scudiero D A, Monks A, Hursey M L, Czerwinski M J, Fine D L, et al. Feasibility of drug screening with panels of human tumor cell lines using a microculture tetrazolium assay. Cancer Res 1988; 48:589-601). MTT (Sigma, St Louis, Mo., USA) was dissolved in PBS in a concentration of 5 mg/ml, filter sterilized, and stored at 4° C. MTT (50 μl of stock solution) was added to each culture and incubated for 3 h at 3TC to allow metabolization. Formazan crystals were solubilized by DMSO (100 μl). Absorbance of the converted dye was measured at a wavelength of 540nm on ELISA reader (BioTek, Winooski, Vt., USA).

The mean concentrations of each compound that generated 50% or total (100%) growth inhibition ($GI_{50}$ and TGI, respectively) as well as the compound concentrations that produced cytotoxicity against 50% of the cultured cells [(half maximal inhibitory concentration ($IC_{50}$)] were calculated using the linear regression method. Using seven absorbance measurements [time 24 h (Ct24), control growth 72 h (Ct72), and test growth in the presence of drug at five concentration levels (Tt72x)], the percentage of growth was calculated at each level of the drug concentrations. The percentage growth inhibition was calculated according to National Cancer Institute (NCI) as:

$$[(i\ Tt72x)-(Ct24)/(Ct72)-(Ct24)]\times100\ \text{for concentrations for which}\ Tt72x>Ct24\ \text{and}\ [(Tt72x)-(Ct24)/Ct24]\times100\ \text{for concentrations for which}\ Tt72x<Ct24$$

GI50: The mean concentration that causes 50% inhibition of cell growth (Growth Inhibition 50%). The calculation of the value is based on the formula:

$$(Tt72x)-(Ct24)/(Ct72)-(Ct24)\times100=50$$

TGI: The mean concentration that causes 100% inhibition of cell growth (Total Growth Inhibition). The value is calculated according to the formula:

$$(Tt72x)-(Ct24)/(Ct72)-(Ct24)\times100=0$$

IC50: The mean concentration that kills 50% of the cells (Inhibition Concentration 50%). The value is calculated according to the formula:

$$(Tt72x)-(Ct24)/(Ct24)\times100=50$$

Results

The results were analyzed with Student's t-test. $P<0.05$ was considered to be statistically significant.

The results of the in vitro study are presented in Table 2.

TABLE 2

|  | Comp. | GI50 (μM) | TGI (μM) | IC50 (μM) |  | GI50 (μM) | TGI (μM) | IC50 (μM) |  | GI50 (μM) | TGI (μM) | IC50 (μM) |
| --- | --- | --- | --- | --- | --- | --- | --- | --- | --- | --- | --- | --- |
| UWB1.289 + BRCA1 | TS53 | 12 | 28 | 42 | OVCAR-3 | 5 | 12 | 25 | SKOV-3 | 8 | 16 | 32 |
|  | TS63 | 8 | 64 | >100 |  | 3 | 32 | >100 |  | 8 | 38 | >100 |
|  | TS62 | 8 | 64 | >100 |  | 8 | 68 | >100 |  | 12 | 56 | >100 |
|  | TS50 | 16 | >100 | >100 |  | 5 | 86 | >100 |  | 6 | >100 | >100 |
|  | TS66 | >100 | >100 | >100 |  | 24 | >100 | >100 |  | 20 | >100 | >100 |
|  | TS167 | 76 | >100 | >100 |  | 65 | >100 | >100 |  | 80 | >100 | >100 |
|  | TS71 | 90 | >100 | >100 |  | 97 | >100 | >100 |  | >100 | >100 | >100 |
|  | TS57 | 85 | >100 | >100 |  | 95 | >100 | >100 |  | >100 | >100 | >100 |
|  | TS22 | 16 | >100 | >100 |  | 90 | >100 | >100 |  | 60 | 100 | >100 |
|  | TS25 | 5 | 12 | 36 |  | 24 | 68 | 94 |  | 18 | 52 | 80 |
|  | TS29 | 10 | 64 | >100 |  | 74 | >100 | >100 |  | 45 | 84 | >100 |
|  | TS26 | 11 | 37 | 54 |  | 41 | 87 | >100 |  | 38 | 72 | >100 |

TABLE 2-continued

|  | Comp. | GI50 (μM) | TGI (μM) | IC50 (μM) |  | GI50 (μM) | TGI (μM) | IC50 (μM) |  | GI50 (μM) | TGI (μM) | IC50 (μM) |
|---|---|---|---|---|---|---|---|---|---|---|---|---|
| UWB1.289 | TS53 | 12 | 56 | >100 | MCF-7 | 15 | 45 | >100 | T-47D | 8 | 37 | >100 |
|  | TS63 | 30 | 50 | >100 |  | 22 | 50 | >100 |  | 27 | 55 | >100 |
|  | TS62 | 13 | >100 | >100 |  | 18 | >100 | >100 |  | 24 | >100 | >100 |
|  | TS50 | 30 | >100 | >100 |  | 40 | >100 | >100 |  | 28 | >100 | >100 |
|  | TS66 | >100 | >100 | >100 |  | >100 | >100 | >100 |  | >100 | >100 | >100 |
|  | TS167 | 56 | >100 | >100 |  | 65 | >100 | >100 |  | 52 | >100 | >100 |
|  | TS71 | >100 | >100 | >100 |  | >100 | >100 | >100 |  | >100 | >100 | >100 |
|  | TS57 | >100 | >100 | >100 |  | >100 | >100 | >100 |  | >100 | >100 | >100 |
|  | TS22 | 88 | >100 | >100 |  | 24 | 90 | >100 |  | 48 | 97 | >100 |
|  | TS22 | 16 | >100 | >100 |  | 90 | >100 | >100 |  | 60 | 100 | >100 |
|  | TS25 | 2 | 4 | 60 |  | 16 | 51 | 86 |  | 12 | 34 | 76 |
|  | TS29 | 10 | 67 | >100 |  | 66 | >100 | >100 |  | 48 | 86 | >100 |
|  | TS26 | 8 | 21 | 72 |  | 25 | 67 | >100 |  | 78 | >100 | >100 |
| PC-3 | TS53 | 12 | 31 | 85 | MOLT-4 | 4 | 21 | 36 | A-549 | 9 | 24 | 58 |
|  | TS63 | 20 | 45 | >100 |  | 6 | 45 | 78 |  | 14 | 36 | 92 |
|  | TS62 | 27 | >100 | >100 |  | 7 | 55 | >100 |  | 15 | 71 | >100 |
|  | TS50 | 44 | >100 | >100 |  | 10 | >100 | >100 |  | 35 | >100 | >100 |
|  | TS66 | >100 | >100 | >100 |  | 85 | >100 | >100 |  | >100 | >100 | >100 |
|  | TS167 | 62 | >100 | >100 |  | 42 | >100 | >100 |  | 74 | >100 | >100 |
|  | TS71 | >100 | >100 | >100 |  | 55 | >100 | >100 |  | >100 | >100 | >100 |
|  | TS57 | >100 | >100 | >100 |  | 94 | >100 | >100 |  | >100 | >100 | >100 |
|  | TS22 | >100 | >100 | >100 |  | 72 | >100 | >100 |  | 45 | 95 | >100 |
|  | TS25 | 8 | 24 | 69 |  | 16 | 29 | 78 |  | 11 | 56 | 87 |
|  | TS29 | 85 | >100 | >100 |  | 61 | >100 | >100 |  | 30 | 71 | >100 |
|  | TS26 | 19 | 47 | 86 |  | 32 | 81 | >100 |  | 20 | 90 | >100 |

The 12 derivatives of 1,2,4,triazolo-[3,4-b]-1,3,4- thiadiazole TS167, TS70, TS61, TS60, TS59, TS58, TS51, TS56, TS54, TS55, TS52, TS65 exhibit a potent cytostatic (IG50<100 μM) than cytotoxic anticancer activity at the concentration tested, with 1050 >100 μM in all 9 human cancer cell lines.

EXAMPLE 4

In Vivo study of toxicity in C57BI/6 mice

In vivo Acute Toxicity

The acute toxicity of the compounds was assessed from lethality by testing different concentrations, starting at 100mg/kg. The therapeutic dose of tested compound is defined as LD10 (lethal dose for 10% of animals). For intraperitoneal (i.p.) treatment, stock solutions of the tested compounds were prepared immediately before use. They were suspended in corn oil in the desired concentration following initial dissolution in 10% dimethylsulfoxide (DMSO). C57BI/6 male and female were used for toxicity studies. Mice were kept under conditions of constant temperature and humidity in sterile cages with water and food.

The results from acute toxicity study are presented in Table 3.

TABLE 3

| Compound | LD50 (mg/kg) | LD10 (mg/kg) |
|---|---|---|
| TS53 | 375 | >500 |
| TS63 | 430 | >500 |
| TS62 | 480 | >500 |
| TS25 | 345 | >500 |
| TS26 | 365 | >500 |
| TS50 | >500 | >500 |
| TS66 | >500 | >500 |
| TS167 | >500 | >500 |
| TS71 | >500 | >500 |
| TS57 | >500 | >500 |

It is notable that all the compounds produced relatively very low acute toxicity on C57BI/6 mice. All LD10s from the i.p. administration of the tested 1,2,4 triazolo-[3,4-b]-1, 3,4 thiadiazole derivatives were over 350 mg/kg whereas LD50s were not reached in any case. For the derivatives TS50, TS66, TS167, TS71, TS57, TS167, TS70, TS61, TS60, TS59, TS58, TS51, TS56, TS54, TS55, TS52 and TS65, acute toxicity was not demonstrated at the higher of the i.p. administrated dosage and LD10 s and LD50 s were not reached (>500 mg/kg).

The invention claimed is:

1. A compound of formula (I) or a pharmaceutically acceptable salt thereof:

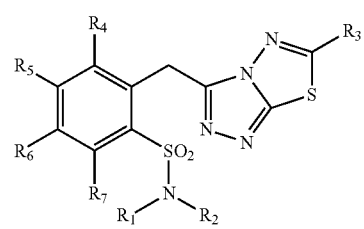

wherein $R_1$ and $R_2$ are the same or different and are selected from the group consisting of $C_1$-$C_5$ alkyl, phenyl, methylphenyl, $R_3$ is selected from the group consisting of:

$CH_2R_8$, $CH_2CH_2R_8$, $CH=CHR_8$, $CH_2CH_2CH_2R_8$, $CH_2CH=CHR_8$, $CH=CHCH_2R_8$, $CH=CH-OR_8$, $CH_2-OR_8$, $CH_2CH_2-OR_8$, $CH=CH-NHR_8$, $CH_2-NHR_8$, $CH_2CH_2-NHR_8$, $CH=CH-SR_8$, $CH_2-SR_8$, $CH_2CH_2-SR_8$,

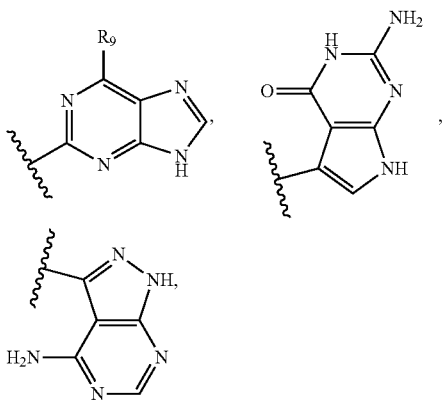

substituted or unsubstituted phenyl, benzyl, pyridyl, pyrimidinyl, triazinyl, triazinanyl, oxazinyl, oxazinanyl, cycloexanyl, cycloexenyl, cycloexadienyl, pyranyl, oxathianyl, piperldinyl, cyclopentanyl, cyclopentenyl, cyclopentadienyl, pyrrolidinyl, pyrrolyl, furanyl, oxazolidinyl, pyrazolidinyl, thlophenyl, oxathiinyl, oxathiolyl, oxathiolanyl, wherein the substituent or substituents are selected from the group consisting of methyl, F, Cl, Br, I, $NO_2$, CN, $NH_2$, $OCH_2X$, $CH_2X$, $CX_3$, $CH_2CH_2X$, OH, wherein X is selected from the group consisting of H, F, Cl, Br, I, $R_4$, $R_5$, $R_6$, $R_7$ are the same or different and selected from the group consisting of:

H, F, Cl, Br, I, $NO_2$, CN, $NH_2$, $OCH_3$, OH, $NHCH_2CH_3$, $N(CH_3)_2$, $R_8$ is selected from the group consisting of:

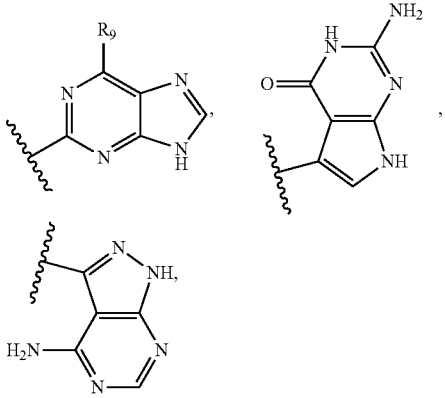

substituted or unsubstituted phenyl, benzyl, pyridyl, pyrimidinyl, triazinyl, triazinanyl, oxazinyl, oxazinanyl, cycioexanyl, cycloexenyl, cycloexadienyl, pyranyl, oxathianyl, piperidinyl, cyclopentanyl, cyclopentenyl, cyclopentadienyl, pyrrolidinyl, pyrrolyl, furanyl, oxazolidinyl, pyrazolidinyl, thiophenyl, oxathiinyl, oxathiolyl, oxathiolanyl, wherein the substituent or substituents are selected from the group consisting of: methyl, F, Cl, Br, I, $NO_2$, CN, $NH_2$, $OCH_2X$, $CH_2X$, $CX_3$, $CH_2CH_2X$, OH, wherein X is selected from the group consisting of H, F, Cl, Br, I, $R_9$ is selected from the group consisting of: $NHR_{10}$, $NR_{11}R_{12}$, $R_{10}$ is selected from the group consisting of: $C_1$-$C_5$ alkyl, phenyl, $R_{11}$ and $R_{12}$ are the same or different and are $C_1$-$C_5$ alkyl.

2. The compound according to claim 1, wherein $R_1$ and $R_2$ are the same or different and are selected from the group consisting of: $C_1$-$C_3$ alkyl, phenyl, methyphenyl.

3. The compound according to claim 1 wherein $R_1$ and $R_2$ are methyl.

4. The compound according to claim 1, wherein $R_3$ is selected from the group consisting of: $CH_2R_8$, $CH_2CH_2R_8$, $CH=CHR_8$, $CH_2CH_2CH_2R_8$, $CH_2CH=CHR_8$, $CH=CHCH_2R_8$,

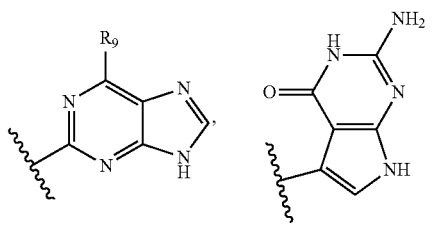

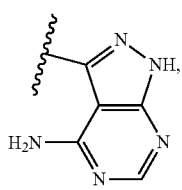

substituted or unsubstituted phenyl, benzyl, pyridyl, wherein the substituent or substituents are selected from the group consisting of methyl, F, Cl, Br, I, $NO_2$, CN, $NH_2$, $OCH_2X$, $CH_2X$, $CX_3$, $CH_2CH_2X$, OH, wherein X is selected from the group consisting of: H, F, Cl, Br, I.

5. The compound according to claim 1, wherein $R_3$ is selected from the group consisting of: $CH=CHR_8$, $CH_2CH_2CH_2R_8$,

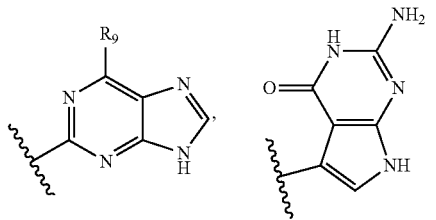

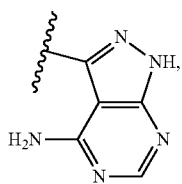

substituted or unsubstituted phenyl, pyridyl, wherein the substituent or substituents are selected from the group consisting of: F, Cl, $NO_2$.

6. The compound according to claim 1, wherein $R_4$, $R_5$, $R_6$, $R_7$ are the same or different and are selected from the group consisting of: H, Cl, Br, I, $NH_2$, $OCH_3$.

7. The compound according to claim 1, wherein $R_4$ and $R_7$ are H, $R_5$ and $R_6$ are $OCH_3$.

8. The compound according to claim 1, wherein $R_8$ is selected from the group consisting of:

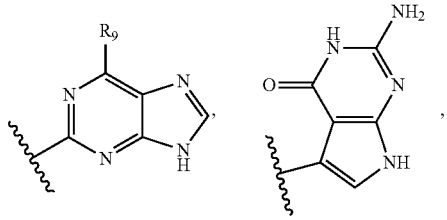

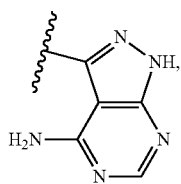

substituted or unsubstituted phenyl, benzyl, pyridyl, wherein the substituent or substituents are selected from the group consisting of: methyl, F, Cl, Br, I, $NO_2$, CN, $NH_2$, $OCH_2X$, $CH_2X$, $CX_3$, $CH_2CH_2X$, OH, wherein X is selected from the group consisting of: H, F, Cl, Br, I.

9. The compound according to claim 1, wherein $R_8$ is selected from the group consisting of:

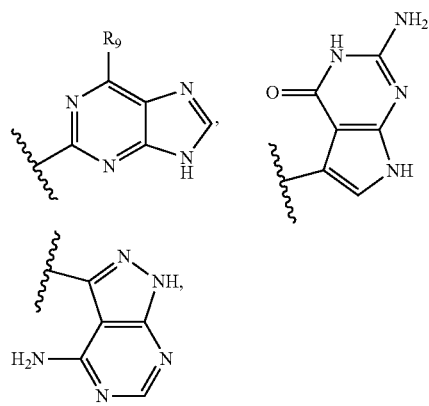

substituted or unsubstituted phenyl, pyridyl, wherein the substituent or substituents are selected from the group consisting of: F, Cl, $NO_2$.

10. The compound according to claim 1, wherein $R_{10}$ is selected from the group consisting of: $C_1$-$C_3$ alkyl, phenyl.

11. The compound according to claim 1, wherein $R_{10}$ is methyl.

12. The compound according to claim 1, wherein $R_{11}$ and $R_{12}$ are the same or different and are $C_1$-$C_3$ alkyl.

13. The compound according to claim 1, wherein $R_{11}$ and $R_{12}$ are methyl.

14. The pharmaceutical composition comprising a compound of formula (I) according to claim 1 or a pharmaceutically acceptable salt thereof and a pharmaceutically acceptable carrier.

15. The compound according to claim 1 or a pharmaceutically acceptable salt thereof for use in the treatment of one of ovarian cancer, breast cancer, prostate cancer, leukemia, or lung cancer.

* * * * *